(12) United States Patent
Gao et al.

(10) Patent No.: US 9,716,240 B2
(45) Date of Patent: Jul. 25, 2017

(54) HIGH MOLECULAR EXTINCTION COEFFICIENT METAL DYES

(75) Inventors: Feifei Gao, Changchun (CN); Yuan Wang, Changchun (CN); Jing Zhang, Changchun (CN); Peng Wang, Changchun (CN); Shaik Mohammad Zakeeruddin, Bussigny (CH); Michael Graetzel, St-Sulpice (CH)

(73) Assignee: Ecole Polytechnique Federale de Lausanne (EPFL), Lausanne (CH)

( * ) Notice: Subject to any disclaimer, the term of this patent is extended or adjusted under 35 U.S.C. 154(b) by 1427 days.

(21) Appl. No.: 12/735,942

(22) PCT Filed: Feb. 27, 2009

(86) PCT No.: PCT/IB2009/050800
§ 371 (c)(1),
(2), (4) Date: Nov. 19, 2010

(87) PCT Pub. No.: WO2009/107100
PCT Pub. Date: Sep. 3, 2009

(65) Prior Publication Data
US 2011/0062541 A1    Mar. 17, 2011

(30) Foreign Application Priority Data
Feb. 27, 2008   (CN) .......................... 2008 1 0050401

(51) Int. Cl.
*C07D 401/04*     (2006.01)
*H01L 51/00*      (2006.01)
*C07F 15/00*      (2006.01)
*C09B 57/10*      (2006.01)
*H01G 9/20*       (2006.01)

(52) U.S. Cl.
CPC ...... *H01L 51/0086* (2013.01); *C07F 15/0053* (2013.01); *C09B 57/10* (2013.01); *H01G 9/2013* (2013.01); *H01G 9/2031* (2013.01); *H01G 9/2059* (2013.01); *Y02E 10/542* (2013.01); *Y02E 10/549* (2013.01)

(58) Field of Classification Search
CPC .................................................. C07D 401/04
USPC .................... 548/400; 546/2, 12; 564/256
See application file for complete search history.

(56) References Cited

U.S. PATENT DOCUMENTS 7,321,037 B2 * 1/2008 Wu et al. .......................... 546/10
8,106,198 B2 * 1/2012 Jiang et al. ....................... 546/2

FOREIGN PATENT DOCUMENTS

| EP | 2 053 618 A1 | 4/2009 |
| WO | WO 2007/071792 A1 | 6/2007 |
| WO | WO 2007/091525 A1 | 8/2007 |
| WO | WO 2009/020098 A1 | 2/2009 |
| WO | WO 2009/082163 A2 | 7/2009 |

OTHER PUBLICATIONS

Gao et al., A New Heteroleptic Ruthenium Sensitizer Enhances the Absorptivity of Mesoporous Titania Film for a High Efficiency Dye-Sensitized Solar Cell, Chemical Communications, No. 21, 2008, pp. 2635-2637.*
Chen et al., Advanced Materials, Wiley-VCH Verlag Weinheim, DE, vol. 19, No. 22, Nov. 1, 2007, p. 3888-3891.*
Gao et al., Chem. Commun., 2008, 2635-2637.*
Ga, Feifei et al., A new Heteroleptic Ruthenium Sensitizer Enhances the Absorptivity of Mesoporous Titanium Film for a High Efficiency Dye-Senstitized Solar Cell, Chemical Communications, No. 21, 2008, pp. 2635-2637.
Chen, C-Y et al.; A New Route to Enhance the Light-Harvesting Capability of Ruthenium Complexes for Dye-Sensitized Solar Cells, Advanced Materials, Wiley-VCH Verlag Weinheim,DE, vol. 19, No. 22, Nov. 1, 2007, pp. 3888-3891.
Gao F. et al.; Conjugation of Selenophene with Bipyridine for a High Molar Extenctlon Coefficient Sensitizer in Dye-Sensitized Solar Cells, Inorganic Chemistry, vol. 48, No. 6, 2009, pp. 2664-2669.
Gao, Feifei, Enhance Optical Absorptivity of Nanocrystailine, Journal of American Chemical Society, vol. 130, Jul. 22, 2009, pp. 10720-10728.
Krebs, F.C. et al.; Dye Sensitized Photovoltaic Cells; Attaching Conugated Polymers to Zwitterionic Ruthenium Dyes; Solar Energy Materials and Solar Cells, Elsevier Science Publishers, vol. 90; Jan. 1, 2006, pp. 142-165.
Thomas, Justin et al.; Zinc (II) and Ruthenium (II) Complexes of Novel Fluorene Substituted Terpyridine Ligands; Synthesis, Spectroscopy and Electrochemistry; Journal of the Chinese Chemical Society, Chinese Electronic Periodical Services, China, vol. 49, No. 5, Jan. 1, 2002, pp. 833-840.
Durr, H. et al.; Supramolecular assemblies for light-induced electron-transfer reaction; Journal of Photochemistry and Photobiology; A Chemistry, Elsevier Sequoia, Lausanne, CH, vol. 80, No. 103, May 31, 1994, pp. 341-350.

* cited by examiner

*Primary Examiner* — Yong Chu
*Assistant Examiner* — Sonya Wright
(74) *Attorney, Agent, or Firm* — Taft Stettinius & Hollister LLP

(57) ABSTRACT

The present invention relates to novel compounds that are useful as ligands in organometallic dyes. More particularly, the invention relates to dyes comprising the compounds, said dyes being sensitizing dyes useful in solar cell technology. According to an embodiment, the present invention discloses new ruthenium dyes and their application in dye-sensitized solar cells (DSC). The referred ruthenium dyes with new structural features can be easily synthesized, show more than 85% light-to-electricity conversion efficiency and a higher than 9% cell efficiency.

7 Claims, 4 Drawing Sheets

HIGH MOLECULAR EXTINCTION COEFFICIENT METAL DYES

This application claims the benefits under 35 U.S.C. 119(a)-(d) or (b), or 365(b) of International Application No. PCT/IB2009/050800 filed 27 Feb. 2009, and China Patent Application No. 200810050401.2, filed 27 Feb. 2008.

TECHNICAL FIELD

The present invention relates to ligands of dyes, in particular of organometallic dyes, that can be used as sensitizers. Furthermore, the present invention relates to the field of photoelectric conversion devices, in particular dye-sensitized solar cells (DSC).

PRIOR ART AND THE PROBLEM UNDERLYING THE INVENTION

The use of conventional fossil fuels as energy resource poses well-known environmental problems, as well as problems of shortage in the medium to long term. In order to solve the approaching energy crisis, a variety of attempts have been performed. Among the available alternatives, the solar energy, used in photovoltaic cells, is almost unlimited and environment-friendly compared to other forms of energy. The silicon solar cell dominates the photovoltaic business due to the high light-to-electricity conversion efficiency and due to the fact that the technology developed for many decades, is mature. However, silicon solar cells suffer from the disadvantages of a high cost of the production process, expensive raw materials and the difficulty of further increasing the efficiency of the cells.

Dye sensitised solar cells (DSCs) make use of photosensitive dye molecules (sensitizers) and transition metal oxides, which perform the functions of absorbing visible light, producing electron-hole couples, and transporting the electron produced by light absorption, respectively. DSCs have many advantages, such as high efficiency, low production cost, low energy consumption during manufacturing, and environmental friendly production. These properties have given these cells high prospects in the photovoltaic business. In 1991, Prof. Michael Grätzel at the École Polytechnique Fédérale de Lausanne developed a technological breakthrough in these cells. Since then, DSCs have gradually become a research topic of high interest in the field of solar cells (Nature 1991, 353, 737).

The dyes used as sensitizers in DSCs are key elements and have a significant impact on stability as well as the device performance, in particular the efficiency. DSCs based on bipyridine ruthenium dyes have been developed significantly (P. Wang, C. Klein, R. Humphry-Baker, S. M. Zakeeruddin and M. Grätzel, J. Am. Chem. Soc., 2004, 127, 808.).

In view of the above, it is an objective of the present invention to provide dyes that are useful as sensitizers in DSCs, and which improve device characteristics such as conversion efficiency.

In particular, it is an objective to provide dyes having high molar extinction coefficients, thus absorbing more light per dye molecule or per molar concentration. In this way, it is hoped to convert more light of the solar spectrum into electrical energy.

It is an objective of the present invention to prepare dyes that are capable of providing a dense monolayer on the semiconductor and/or photoelectrode surface of a dye-sensitized solar cell. A dense arrangement of the dye molecules on said surface is expected to increase light absorption and reduce the risk of corrosion and other kind of abrasion of the semiconductor and/or photoelectrode surface. In general, it is an objective to increase long term stability of the solar cell. A dense arrangement of dye molecules also allows a reduction of the porosity of the surface an also of the overall thickness of the semiconductor layer at the photoanode, Another objective to provide a dye that, when absorbed on a semiconductor is capable of a absorbing as much light of the solar spectrum as possible. In particular, it is an objective to provide dyes that exhibit a pronounced red-shift when absorbed on the photoelectrode and/or semiconductor surface. It is an objective to provide a dye absorbing more photons in the red spectrum of light.

Generally, it is an objective of the present invention to provide dyes having an increased propensity of arranging and/or being adsorbed on a semiconductor and/or photoelectrode surface of a dye-sensitized solar cell in a manner that positively affects the characteristics of the device, such as conversion efficiency, for example. In other words, it is an objective to judiciously arrange of dye molecules on the photoanode surface by the molecular designing of the structures of such dyes.

Generally, the present invention addresses the objectives of providing new dyes with low production cost, and high stability, resulting in photovoltaic conversion devices having improved characteristics, such as high energy conversion efficiency.

The present invention addresses the problems depicted above.

SUMMARY OF INVENTION

The present inventors provide novel compounds useful in the preparation of dyes, as well as the dyes comprising these compounds as ligands. Remarkably, the dyes obtained according to the invention have high molar extinction coefficients. The compounds disclosed are useful in the preparation of sensitizing dyes of DSCs.

Surprisingly, it is observed that the dyes of the present invention show a particularly pronounced strong red-shift response when absorbed on the photoelectrode surface, typically a TiO$_2$ surface. In this way more light in the red spectrum of solar light can be utilized for the generation of electricity.

Furthermore, without wishing to be bound by theory, a high degree in stacking is observed with the dyes of the present invention when absorbed on a photoelectrode and/or semiconductor surface. Accordingly, dye molecules are absorbed in a very densely and tightly, in an ordered arrangement. In the ordered arrangement, dye molecules are arranged next to each other with aromatic rings of the antenna ligand of the dyes being in a π-stacked, superimposed relationship. In this way, a particularly dense arrangement is obtained, which further increases light absorption per surface area.

Without wishing to be bound by theory, the inventors believe that the π-stacking interaction can be positively influenced by using, in the antenna ligand (also known as ancillary ligand) a system of condensed rings, such as condensed thiophene rings. For example, by using a bipyridine ligand substituted with a substituted thieno[3,2-b]thiophenyl, the planarity of the ligand is increased and a increased stacking can be obtained. A dense layer obtained by π-stacking may also be obtained with antenna ligands based on a bipyridine substituted with chains of aromatic rings comprising and not comprising heteroatoms. Due to the dense stacking of the dye molecules on the photoelectrode and/or semiconductor surface, the thickness of the dye-carrying layer and/or the porosity can be reduced while still maintaining a high light absorption.

Accordingly, in an aspect, the present invention provides bipyridine compounds, which are substituted with one or more aromatic hydrocarbons comprising at least one heteroatom.

According to another aspect, the present invention provides compounds of formula (1):

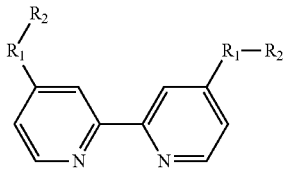

(1)

wherein $R_1$ represents a group which comprises one or more aromatic hydrocarbon moieties selected from the group of moieties of formulae (2) to (33), and preferably (2)-(13), or a combination of two or more thereof:

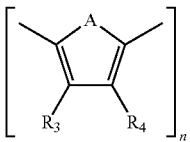

(2)

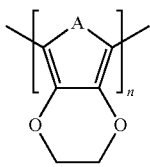

(3)

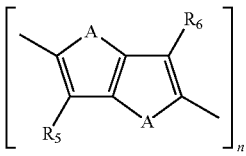

(4)

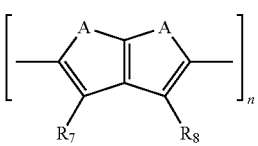

(5)

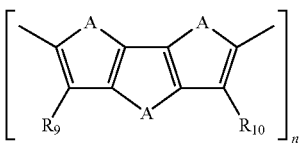

(6)

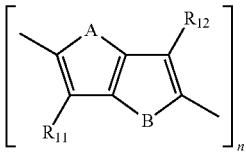

(7)

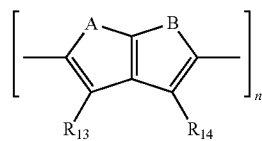

(8)

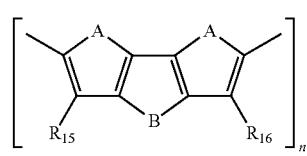

(9)

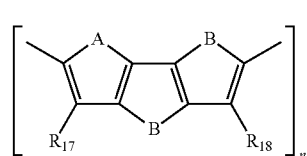

(10)

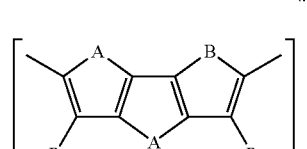

(11)

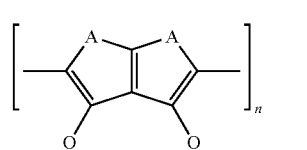

(12)

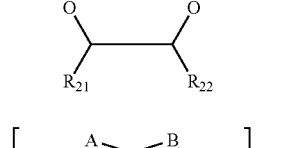

(13)

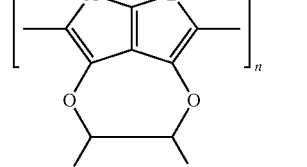

(14)

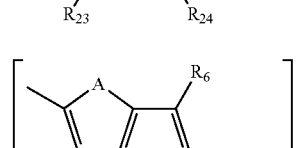

(15)

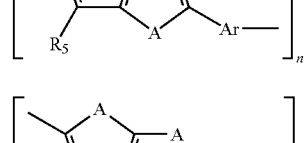

(16)

(17) 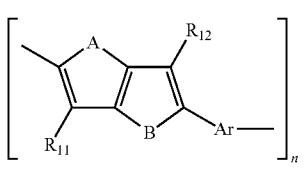
(18) 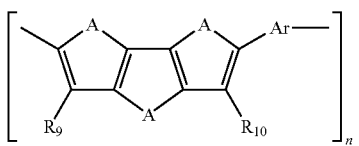
(19) 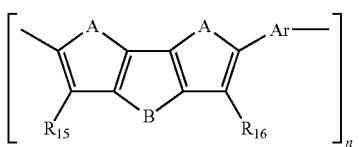
(20) 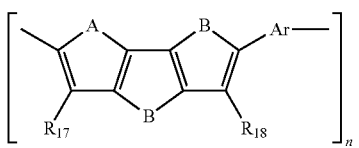
(21) 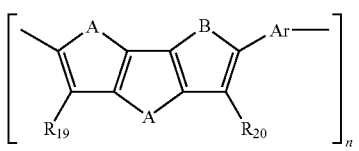
(22) 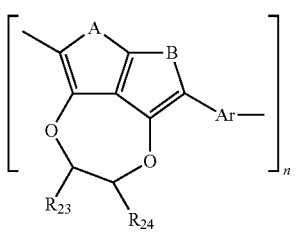
(23) 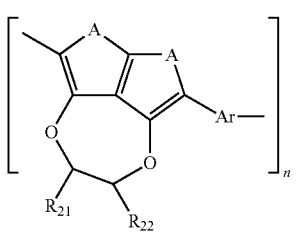
(24) 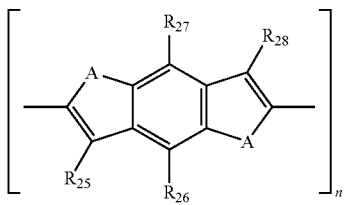
(25) 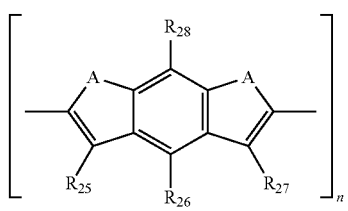
(26) 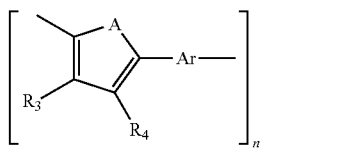
(27) 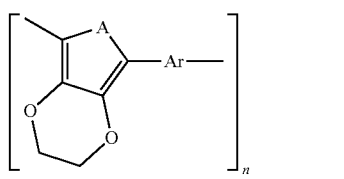
(28) 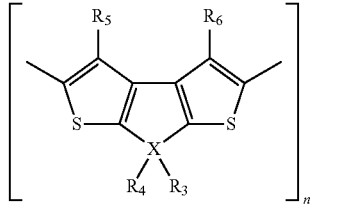
(29) 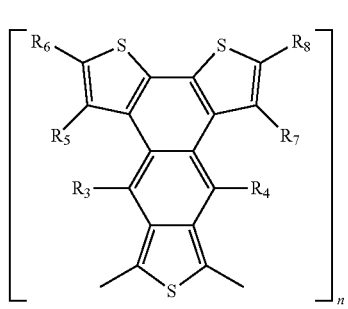
(30) 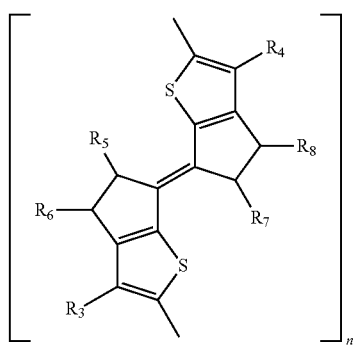

-continued

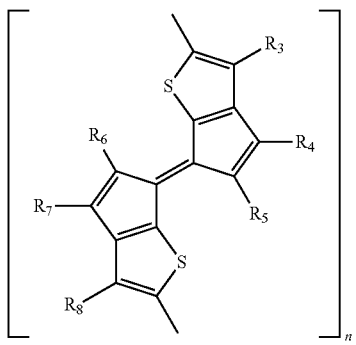

(31)

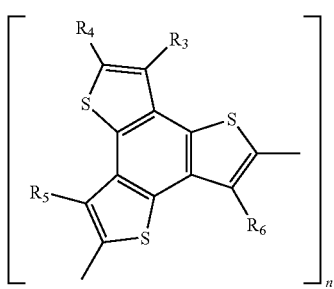

(32)

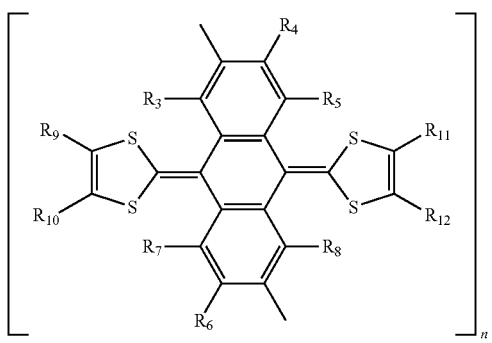

(33)

wherein, if $R_1$ comprises only the moiety (3), n for (3) is ≥2, and for all other $R_1$ and with all other combinations of moieties (2)-(33) n is ≥1;

wherein A represents O or S; B represents O or S, the said A and B being selected independently one from the other, with the proviso that in a compound where $R_1$ is only (2), n is 1 and $R_2$ is alkyl, A is O;

wherein, in moiety (28), X is selected from any one of C, Si, Ge, Sn or Pb;

wherein substituents $R_2$ represent, independently, hydrogen (H), halogen, hydroxyl, sulfhydryl, nitryl (—CN), cyanate, isocyanate, amine, acyl, carboxyl, sulfinyl, alkyl, alkenyl, alkynyl, and aryl, wherein said alkyl, alkenyl, alkynyl may be linear, branched or cyclic, and wherein said amine, acyl, carboxyl, sulfinyl, alkyl, alkenyl, alkynyl, and aryl may be further substituted, and wherein one or more carbon atom, for example one or more methylene carbon atom, in said alkyl, alkenyl, alkynyl, and aryl may be replaced by any heteroatom and/or group selected from the group of —O—, —C(O)—, —C(O)O—, —S—, —S(O)—, $SO_2$—, —S(O)$_2$O—, —N═, —P═, —NR'—, —PR'—, —P(O)(OR')—, —P(O)(OR')O—, —P(O)(NR'R')—, —P(O)(NR'R')O—, P(O)(NR'R')NR'—, —S(O)NR'—, and —S(O)$_2$NR', with R' being H, a C1-C6 alkyl, optionally partially or totally perfluorinated, and/or a phenyl, or a monocyclic aromatic heterocycle, optionally partially or totally perfluorinated;

wherein Ar is a substituted or unsubstituted ar-diyl devoid of any heteroatom; Preferably, Ar comprises from 6 to 25 carbon atoms; Preferably, Ar represents a substituted or unsubstituted phenylene;

wherein $R_3$ to $R_{24}$ represent, independently, hydrogen (H), hydroxyl, alkyl, alkenyl, alkynyl, aryl, alkoxy, aryloxy, aralkyl, alkylthio, alkyl halide or halogen; and, wherein carbon atoms at positions 3, 3', 5, 5' and 6, 6' of the 2,2'-bipyridine structure of formula (1) may be further substituted, said further substituents being defined, independently, as substituents $R_2$ and its preferred substituents, and more preferably as substituents $R_3$-$R_{24}$ and preferred substituents.

In the compounds of formula (1) above, in case two moieties carrying substituent's with identical substituent number, for example a compound comprising moieties (2) and (26) or (2) and (32), both carrying a substituent $R_3$ (and also a substituent $R_4$), said identically numbered substituents may be the same or different. For example, on $R_3$ of (2) may be hydrogen and $R_3$ on (26) in the same compound and even in the same $R_1$ may be methyl.

According to another aspect, the present invention provides the use of the compound of the invention as a ligand in an organometallic compound, as a ligand in a dye, as a ligand in a sensitizing compound, and/or as a ligand in a metal-containing sensitizing dye.

In further aspects, the present invention provides the use of the compounds of the invention as a structural component of a dye and/or as structural a component of an organometallic compound. The invention also provides the use of the compounds of the invention as a structural component of a dye of a dye-sensitized photoelectric conversion device.

In yet another aspect, the present invention provides a dye of formula (35):

$$ML_1L_2(L_3)_2 \quad (35)$$

wherein:

M is a metal atom selected from Ru, Os, Ir, Re, Rh, and Fe;

$L_1$ is a ligand selected from the compounds of the present invention;

$L_2$ is an anchoring ligand;

$L_3$ is a spectator ligand.

The invention also provides the use of the dyes of the invention as a sensitizer in a dye-sensitized photoelectric conversion device.

The dyes of the present invention have several advantages. Their production cost is low, they are obtained in high yield and are easy to purify. Furthermore, the molecular design of the dyes of the invention can be easily modified. In particular, the position of $R_1$ can be easily varied by using the disclosed moieties (2)-(33), preferably (2)-(13), and by selecting any combination comprising two or more of these moieties. More than 85% absorbed light-to-electricity conversion efficiency and higher than 10% overall cell (energy) conversion efficiency are achieved when the exemplary dyes are used as sensitizers in DSCs. The said dyes have thus a good light-to-electricity conversion performance.

DETAILED DESCRIPTION OF THE PREFERRED EMBODIMENTS

Figure 1:
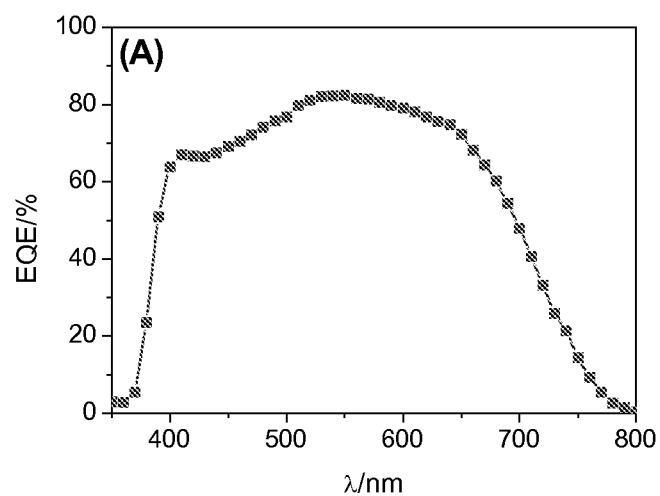
FIG. 1 shows the photocurrent action spectrum of a DSC sensitized with the ruthenium dye (40) according to the present invention.
Figure 2:
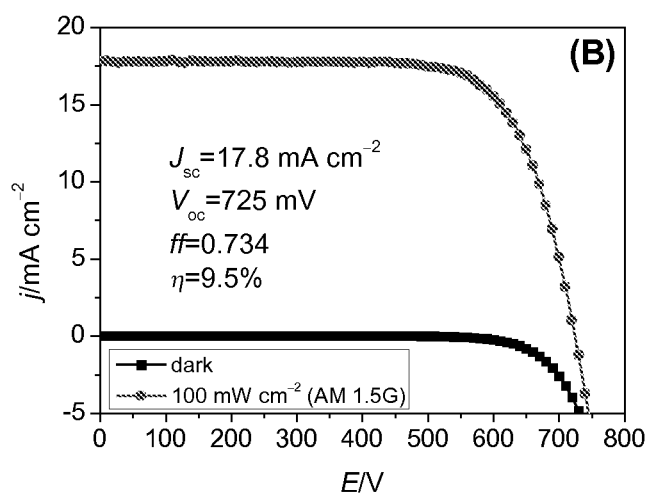
FIG. 2 shows the current density-voltage characteristics of a DSC with the ruthenium dye (40) according to the present invention.
Figure 3:
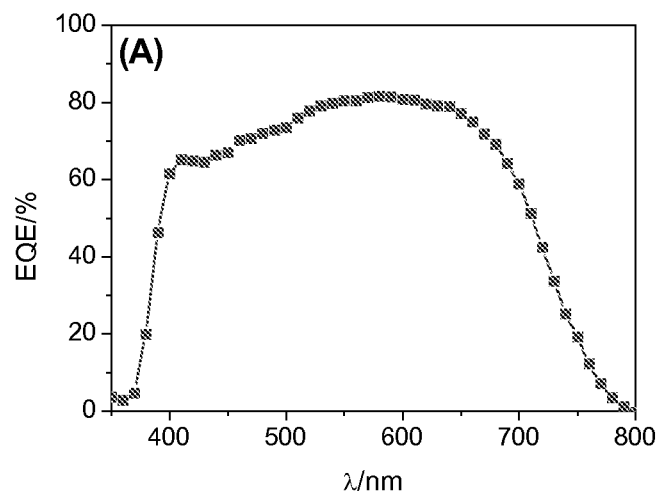
FIG. 3 shows the photocurrent action spectrum of a DSC sensitized with the ruthenium dye (41) according to the present invention.
Figure 4:
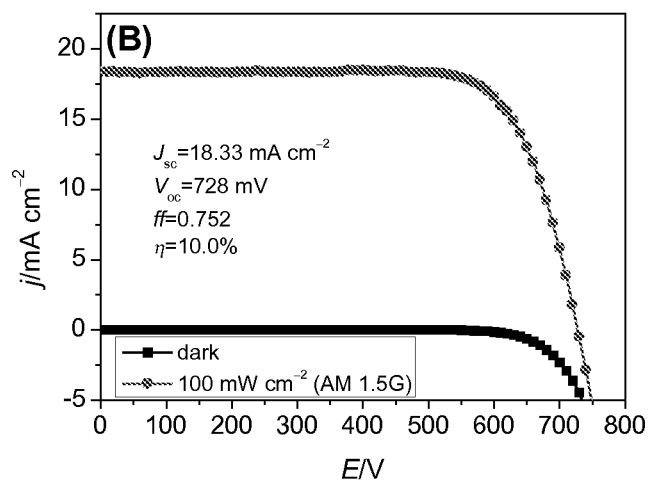
FIG. 4 shows the current density-voltage characteristics of a DSC with the ruthenium dye (41) according to the present invention.
Figure 5:
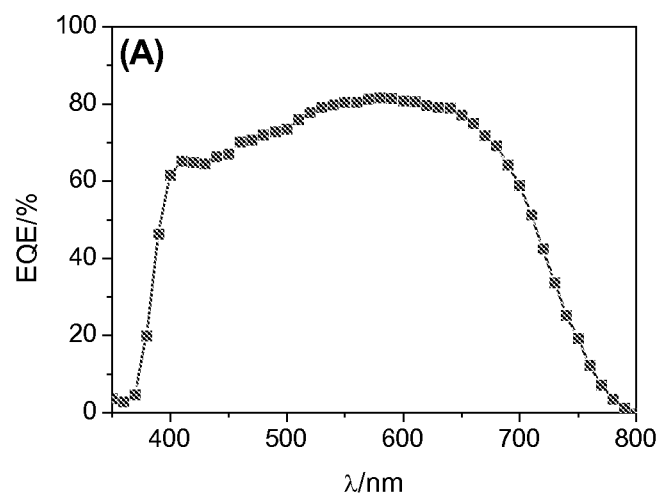
FIG. 5 shows the photocurrent action spectrum of a DSC sensitized with the ruthenium dye (44) according to the present invention.
Figure 6:
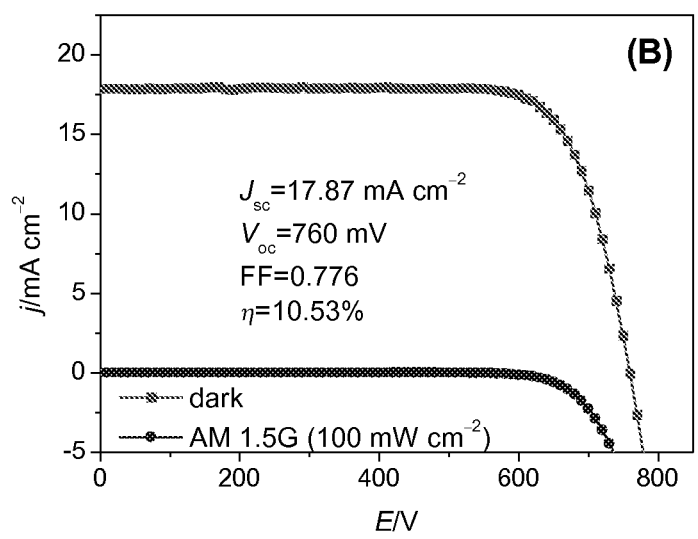
FIG. 6 shows the current density-voltage characteristics of a DSC with the ruthenium dye (44) according to the present invention.

The present invention relates to bipyridine compounds, which are substituted with one or more aromatic hydrocarbons comprising at least one heteroatom. The aromatic hydrocarbon is preferably a further substituted or unsubstituted aryl. According to an embodiment, the heteroatoms provided in said aromatic hydrocarbon are selected from S and O.

The aryl is preferably an aromatic heterocycle or a system of two, three, four or more fused rings, at least one of which is an aromatic ring comprising at least one heteroatom. In the compound of formula (1), the moiety $R_1$ represents the aromatic hydrocarbon, of which the moieties of formulae (2)-(33) represent preferred embodiments.

The substituents of the bipyridine compounds of the invention, that is, any entity —$R_1$-$R_2$, preferably has from 4-50 carbon atoms and 1-30 heteroatoms, more preferably 4-35 carbons and 1-20 heteroatoms, and most preferably 6-25 carbons and 1-10 heteroatoms. Preferred heteroatoms are selected from halogen, Se, O and S, more preferably from O and S.

In a specific moiety (2)-(33) of the compounds of formula (1) according to the invention, A and B may be the same (both O or both S) or different (one O and one S). Preferably, A and B are different, meaning that when A is an oxygen atom, B is a sulphur atom and when A is sulfur, B is oxygen.

In an embodiment, in a compound of formula (1) where $R_1$ is only moiety (2) and $R_2$ is as defined herein, A is O.

In the substituent $R_2$ of the compound of formula (1) above, it is indicated that said amine, acyl, carboxyl, sulfinyl, alkyl, alkenyl, alkynyl, and aryl may be further substituted. Further substituents may be selected from C1-10 alkyl, C2-10 alkenyl, C2-10 alkynyl, which again may be linear, branched or cyclic, and from a mono- or bicyclic C6-C15 aryl. At a carbon atom, further substituent's may also be selected from hydroxyl, sulfhydryl, nitryl, cyanate, and isocyanate. Any alkyl, alkenyl, alkynyl and aryl (also the one of $R_2$, not considering the further substituent) may or may not be partially or totally halogenated.

Preferably, any alkyl, alkenyl and/or alkynyl mentioned herein is linear or branched.

According to a preferred embodiment, substituents $R_2$ represent, independently, hydrogen (H), alkyl, alkoxy, cycloalkyl, alkyl halide, halogen, heterocycle,

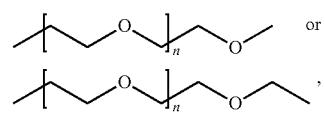

with n≥0; and, $R_3$ to $R_{24}$ represent, independently, hydrogen (H), hydroxyl, alkyl, cycloalkyl, alkoxy, aryloxy, aralkyl, alkylthio, alkyl halide or halogen.

According to an embodiment, the compound of the present invention is selected from a compound of any one of formula (I)-(V) below:

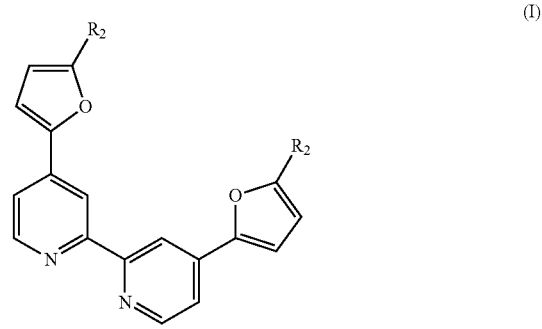

(I)

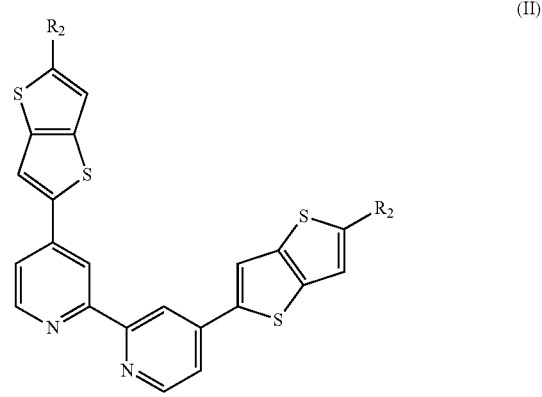

(II)

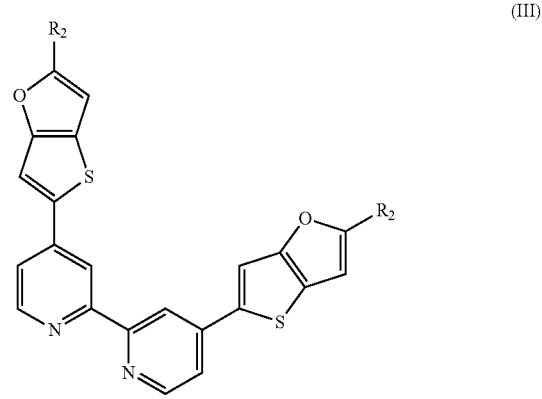

(III)

-continued

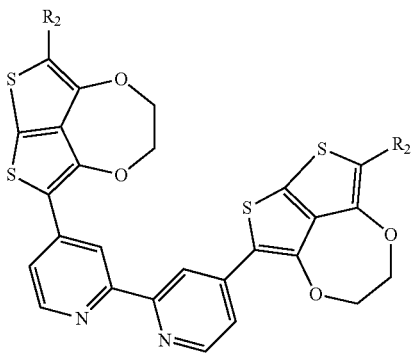
(IV)

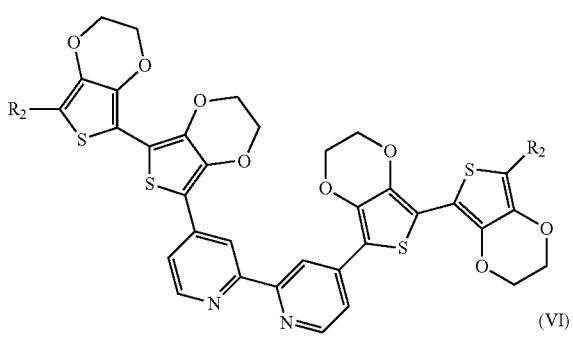
(V)

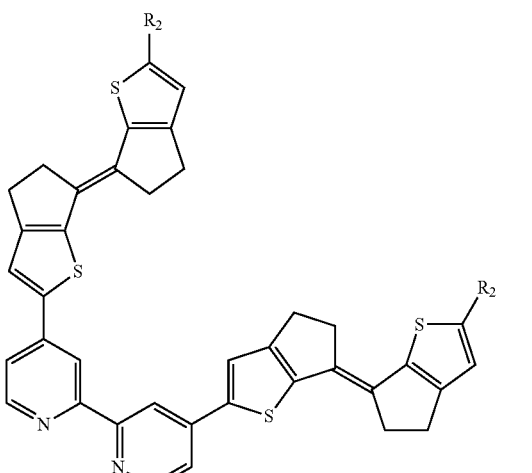
(VI)

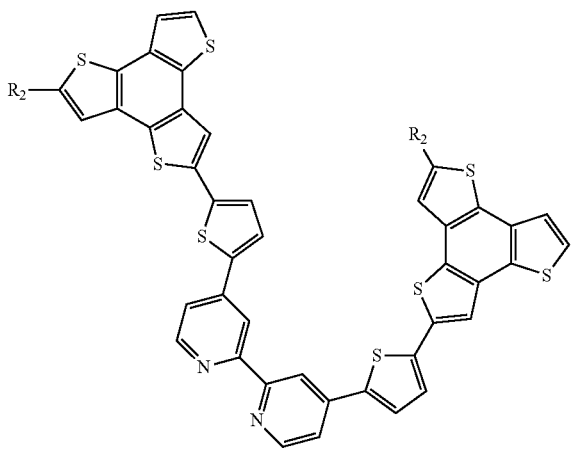
(VII)

wherein $R_2$ is as defined above.

According to an embodiment of the compounds of the invention, $R_2$ comprises from 0-25 carbons and from 0-10 heteroatoms. Preferably, $R_2$ comprises from 1-15 carbons and from 0-5 heteroatoms, more preferably 1-10 carbons and 0-3 heteroatoms, wherein heteroatoms are defined as above for the moiety —$R_1$, —$R_2$.

According to a preferred embodiment, —$R_2$ is an alkyl, an alkenyl, an alkynyl or an aryl, in particular an alkyl, an alkenyl, or an alkynyl.

The compounds of the invention are useful in the preparation of dyes, organometallic compounds and/or of sensitizers. The compounds thus preferably form a structural component of such dyes, organometallic compounds and/or sensitizers, respectively. Preferably, the bipyridine compounds of the invention are used as ligands in dyes, organometallic compounds and/or sensitizers. The dyes, organometallic compounds and/or sensitizers comprising the compounds of the invention may, in turn, be used in photoelectric conversion devices. They may in particular be used as sensitizing dyes in such devices, for example.

The present invention relates to dyes of formula (35):

$$ML_1L_2(L_3)_2 \qquad (35),$$

wherein $L_1$ is a compound according to the invention.

According to a preferred embodiment, M is Ru (ruthenium).

$L_2$ is an anchoring ligand, which has the purpose of anchoring the dye of formula (35) on a surface of choice. Accordingly, the anchoring ligand comprises a structural unit suitable for binding to the metal M and one, two or more anchoring groups. The skilled person will thus select the binding unit and the anchoring group in dependence of the surface to which the overall dye is to be anchored.

According to an embodiment, the anchoring ligand $L_2$ is a bi-pyridine compound of formula (36):

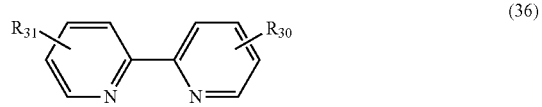
(36)

wherein $R_{30}$ and $R_{31}$ are independently one from the other selected from H, alkyl, alkenyl, alkynyl, aryl, said alkyl, alkenyl and/or aryl being substituted or unsubstituted, and from anchoring groups which may, for example, be selected from —COOH, —PO$_3$H$_2$, —PO$_4$H$_2$, —SO$_3$H$_2$, SO$_4$H$_2$, —CONHOH$^-$, acetylacetonate, deprotonated forms of the aforementioned, and chelating anchoring groups with Π-conducting character; with the proviso that at least one of the substituents $R_{30}$ and $R_{31}$ comprises an anchoring group.

According to an embodiment, one or both of $R_{30}$ and $R_{31}$ can be an alkyl, alkenyl, alkynyl and/or aryl which is substituted with an anchoring group as cited above, for example.

According to another embodiment, $L_2$ is a bi-pyridine ligand of formula (37)

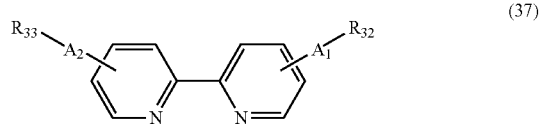
(37)

wherein $A_1$ and $A_2$ are optional and, if present, are independently selected from an aromatic mono- or bicyclic ring system optionally comprising one or more heteroatoms, and $R_{32}$ and $R_{33}$ are independently selected from H and from the anchoring groups —COOH, —$PO_3H_2$, —$PO_4H_2$, —$SO_3H_2$, $SO_4H_2$, —CONHOH$^-$, acetylacetonate, deprotonated forms of the aforementioned, and chelating anchoring groups with Π-conducting character; provided that at least one of $R_{32}$ and $R_{33}$ is an anchoring group. $A_1$ and $A_2$ may thus be absent, in which case at least one anchoring group, $R_{32}$ and/or $R_{33}$, is connected directly to the bipyridine structure of formula (37). Examples for the moieties $A_1$ and $A_2$, if present, are phenyl and thiophene.

Examples of chelating anchoring groups with Π-conducting character are oxyme, dioxyme, hydroxyquinoline, salicylate, and α-keto-enolate groups.

According to an embodiment, the present invention provides organometallic compounds selected from the compounds (40)-(44) below:

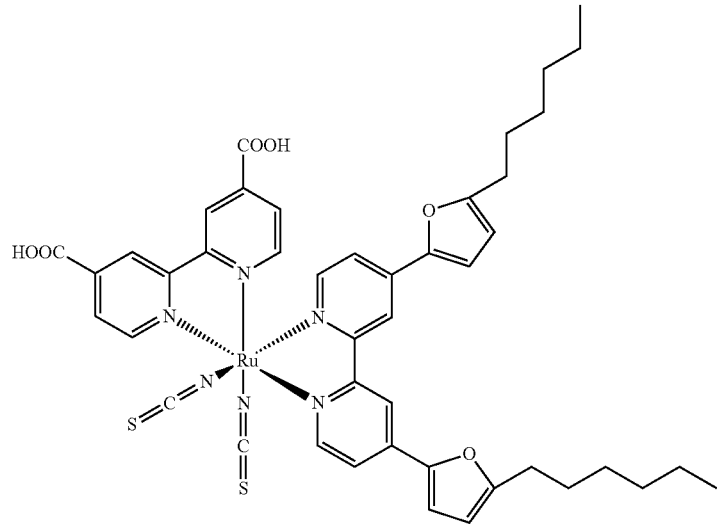

(40)

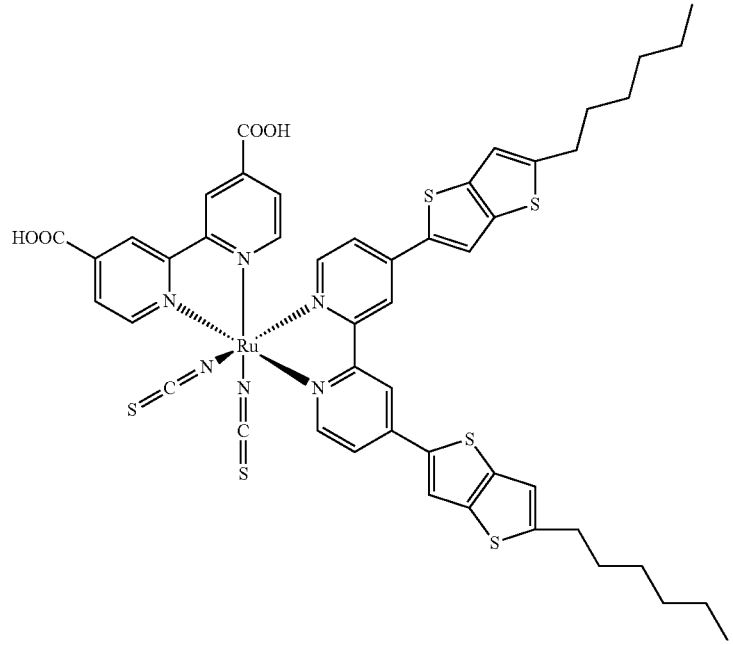

(41)

-continued
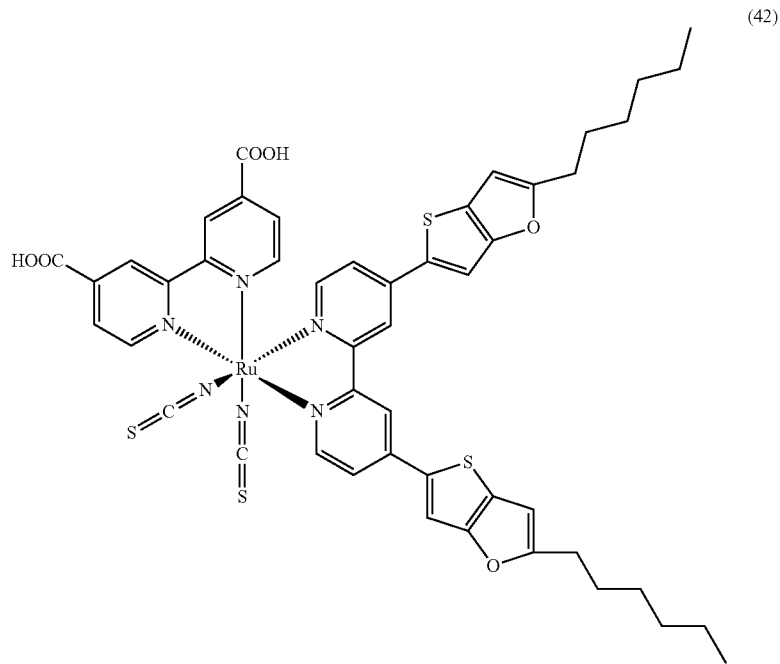
(42)
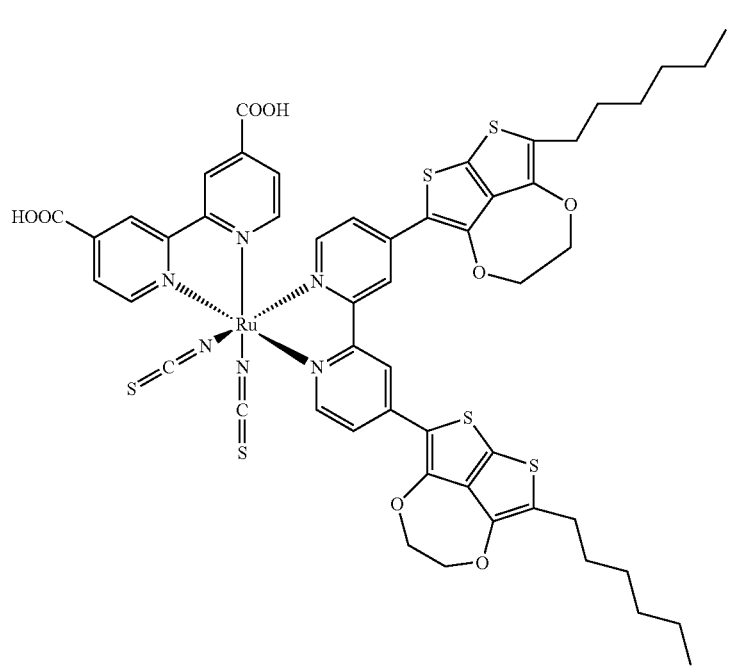
(43)

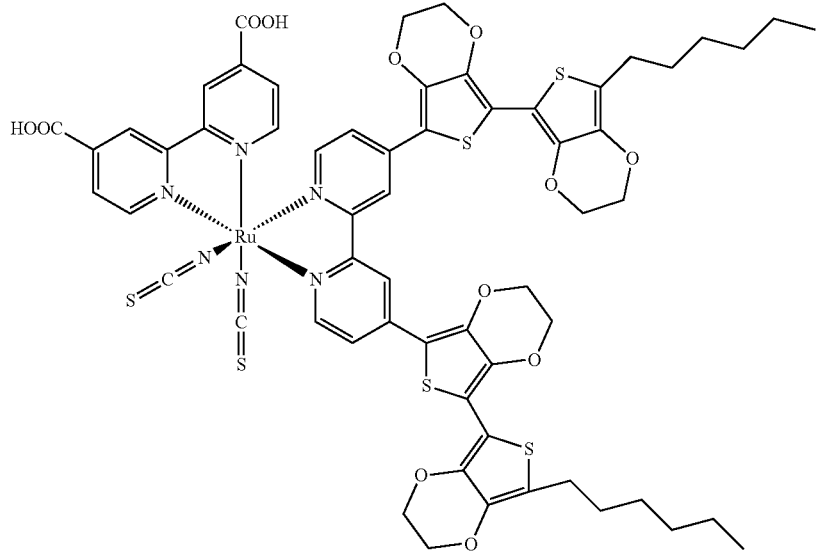

(44)

The present invention relates to the use of dyes and/or organometallic compounds as defined herein as a sensitizer in a dye-sensitized photoelectric conversion device.

The present invention relates to photoelectric conversion devices. The photoelectric conversion device is preferably a photovoltaic cell, in particular a solar cell, capable of converting electromagnetic radiation, in particular visible, infrared and/or UV light, in particular sunlight, into electrical current. According to a preferred embodiment, the photoelectric conversion device is a dye-sensitized conversion device, in particular a dye-sensitized solar cell (DSC). The meanings of the terms "dye", "sensitizer", "sensitising dye" and "dye sensitizer" may partially or totally overlap with each other.

The present invention relates to a photoelectric conversion device comprising a compound, an organometallic compound, a dye, and/or a sensitizer of the invention.

Figure 7:
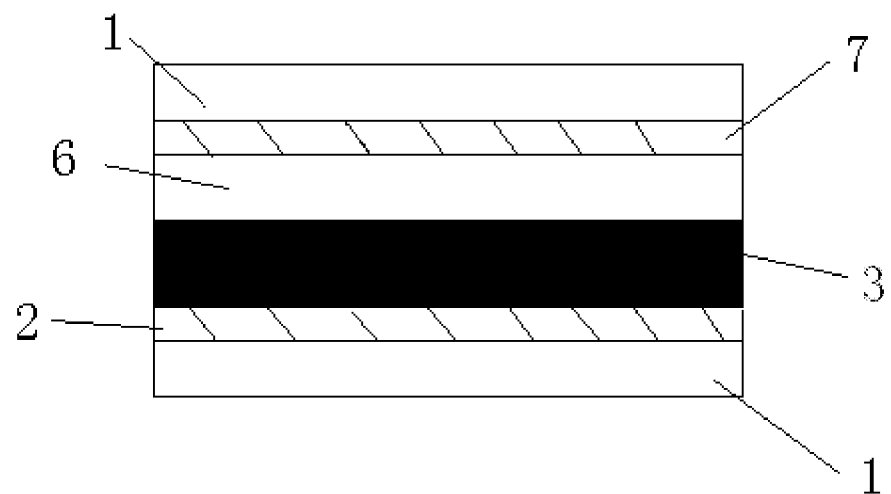
FIG. 7 is a schematic representation of a DSC with a dye according to the present invention.
Figure 8:
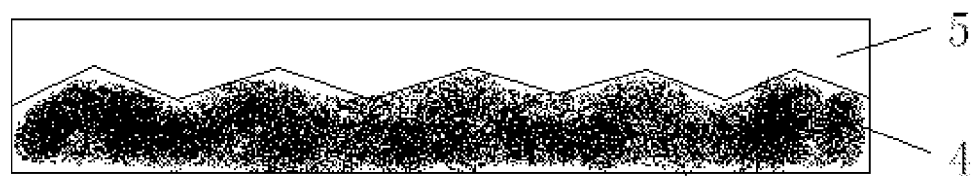
FIG. 8 is a schematic representation of the light adsorption layer 3 shown in FIG. 7, comprising a semiconductor nanoparticle layer 4 and a dye layer 5.

For the purpose of illustration, an exemplary, non-limiting embodiment of a DSC according to the invention is shown in FIGS. 7 and 8. The device comprises a light absorption layer 3 comprising a semiconductor material 4 and, absorbed thereto, a layer 7 comprising a dye according to invention or a dye comprising the compound of the invention.

According to a preferred embodiment, the semiconductor material 4 comprises a porous structure. The porous structure is illustrated by the zigzag line in FIG. 8.

The device of the invention preferably further comprises at least one substrate 1, an electrode 2 and a counter electrode 7, and a charge transport layer 6, said charge transport layer being provided between said counter electrode and said dye layer 5.

The substrate layer 1 is preferably a transparent substrate layer selected from glass or plastic. Although there are two, a top and a bottom substrate layer 1 shown in FIG. 7, devices with only one, a top or a bottom transparent substrate layer are also encompassed. Generally, the substrate is then on the side of the counter electrode 7. Exemplary plastic substrates are polyethylene terephthalate, polyethylene naphthalate (PEN), polycarbonate, polypropylene, polyimide, 3-acetyl cellulose, and polyethersulfone (PES).

The conductive layer 2 may be provided by of one of Indium tin oxide (ITO), tin oxide fluoride (FTO), ZnO—$Ga_2O_3$, ZnO—$Al_2O_3$, tin-oxide, antimony tin oxide (ATO) and zinc oxide, for example.

The device of the present invention comprises a semiconductor layer (4). This layer may be constituted by a single layer or by several layers, generally has an overall thickness of up to 100 μm, for example up to 60 μm. However, according to an embodiment of the present invention, the device of the invention comprises a layer 4 comprising a semiconductor material, wherein said semiconductor layer has a thickness of smaller than 20 μm. The semiconductor layer 4 with a thickness of smaller than 20 microns may also consist of a single layer or comprise two or more separate layers, for example sub-layers. For example, the sub-layers are arranged one above the other, each sub-layer being in continuous contact with the respective one or two neighboring sub-layers. For example, the semiconductor layer may comprise a base semiconductor layer having a comparatively low porosity and thereon a comparatively high porosity semiconductor layer, wherein the sensitizers will preferably or to a larger extent be absorbed on the semiconductor material in the high porosity sub-layer. In other words, the different layers may have different porosity, for example they may be prepared from nanoparticles of different size, but preferably the sizes remain in the ranges given further below. The thickness of the entire semiconductor layer, including all potential sub-layers, is preferably <20 μm, more preferably ≤17 μm, even more preferably ≤15 and most preferably ≤13 μm.

The semiconductor material layer 4 may comprises a semiconductor material selected from Si, $TiO_2$, $SnO_2$, ZnO, $WO_3$, $Nb_2O_5$, and $TiSrO_3$, which all are exemplary semiconductor materials for the purpose of the invention. Preferably, the semiconductor material layer 4 comprises a porous layer made of semiconductor nanoparticles, for example nanoparticles made of the semiconductor materials above. The average diameter of the semiconductor nanoparticles preferably lies in the range of 0.5 nm-2000 nm, preferably 1-1000 nm, more preferably 2-500 nm, most preferably 5-100 nm.

The dye is provided in the form of a dye layer 5, which comprises dye molecules according to the present invention, in particular dyes comprising a compound as defined by formula (1), and/or dyes as defined by formula (35), for example the exemplary dyes according to formulae (40)-(44). The dye molecules are preferably anchored by way of their anchoring group on the surface of the porous nanoparticle layer 4 and form a monomolecular layer thereon.

The charge transport layer 6 preferably comprises (a) an electrically conductive hole and/or electron transporting material or (b) an electrolyte. If the charges are transported by said electrically conductive hole and/or electron transporting material, electrons and/or holes move by electronic motion, instead of diffusion of charged molecules. Such electrically conductive layers are preferably based on organic compounds, including polymers. Accordingly, layer 6 may be an electron and/or hole conducting material. U. Bach et al. "Solid-state dye-sensitized mesoporous $TiO_2$ solar cells with high photon-to-electron conversion efficiencies", Nature, Vol. 395, Oct. 8, 1998, 583-585, disclose the amorphous organic hole transport material 2,2',7,7'-tetrakis (N,N-di-p-methoxyphenyl-amine)9,9'-spirofluorene (OMeTAD) in dye-sensitised solar cells. In WO2007/107961, charge transporting materials, which are liquid at room temperature and their application in dye-sensitized solar cells are disclosed. These materials may be used, for example, for the purpose of the present invention.

If the charge transport layer is an electrolyte, which is preferred, it comprises a redox-couple. Preferred examples of redox couples suitable for dye sensitized solar cells are the $I^-/I_3^-$ couple or the $SeCN^-/Se(CN)_3^-$ redox couple.

The electrolyte preferably comprises one or more ionic liquids. Ionic liquids are generally defined by the fact that they have a melting point of 100° C. or lower. For example, anions of suitable ionic liquids may be selected from $I^-$, $Br^-$, $Cl^-$, $[N(CN)_2]^-$, $[N(SO_2CF_3)_2]^-$, $[PF_6]^-$, $[BF_4]^-$, $[NO_3]^-$, $[C(CN)_3]^-$, $[B(CN)_4]^-$, $[CF_3COO]^-$, $[ClO_4]^-$, $[BF_3CF_3]^-$, $[CF_3SO_3]^-$, $[CF_3F_2SO_3]^-$, $[CH_3H_2SO_3]^-$, $[(CF_3SO_2)_2N]^-$, $[(C_2H_5SO_2)_2N]^-$, $[(CF_3SO_2)_3C]^-$, $[(C_2F_5SO_2)_3C]^-$, $[(FSO_2)_3C]^-$, $[CH_3CH_2OSO_3]^-$, $[CF_3C(O)O]^-$, $[CF_3CF_2C(O)O]^-$, $[CH_3CH_2C(O)O]^-$, $[CH_3C(O)O]^-$, $[P(C_2H_5)_3F_3]^-$, $[P(CF_3)_3F_3]^-$, $[P(C_2H_4H)(CF_3)_2F_3]]^-$, $[P(C_2F_3H_2)_3F_3]^-$, $[P(C_2F_5)(CF_3)_2F_3]^-$, $[P(CF_3)_3F_3]^-$, $[P(C_6H_5)_3F_3]^-$, $[P(C_3H_7)_3F_3]^-$, $[P(C_4H_9)_3F_3]^-$, $[P(C_2H_5)_3F_4]^-$, $[(C_2H_5)_2P(O)O]^-$, $[(C_2H_5)_2P(O)O_2]^{2-}$, $[PC_6H_5]_2F_4]^-$, $[(CF_3)_2P(O)O]^-$, $[(CH_3)_2P(O)O]^-$, $[(C_4H_9)_2P(O)O]^-$, $[CF_3P(O)O_2]^{2-}$, $[CH_3P(O)O_2]^{2-}$, $[(CH_3O)_2P(O)O]^-$, $[BF_2(C_2F_5)_2]^-$, $[BF_3(C_2F_5)]^-$, $[BF_2(CF_3)_2]^-$, $[B(C_2F_5)_4]^-$, $[BF_3(CN)]^-$, $[BF_2(CN)_2]^-$, $[B(CF_3)_4]^-$, $[B(OCH_3)_4]^-$, $[B(OCH_3)_2(C_2H_5)]^-$, $[B(O_2C_2H_4)_2]^-$, $[B(O_2C_2H_2)_2]^-$, $[B(O_2CH_4)_2]^-$, $[N(CF_3)_2]^-$, $[AlCl_4]^-$ and $[SiF_6]^{2-}$.

Cations of ionic liquids according to the invention may, for example, be selected from compounds having structures as shown below:

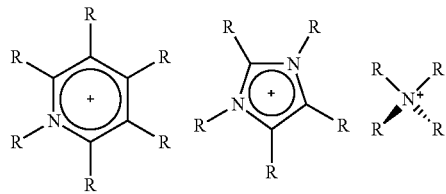

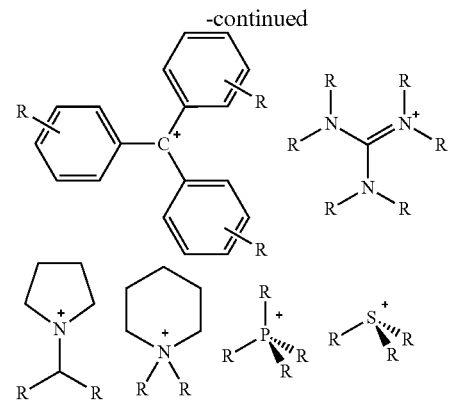

-continued

H, provided that at least one R linked to a heteroatom is different from H;

a linear or branched C1-C20 alkyl;

a linear or branched C2-C20 alkenyl, comprising one or several double bonds;

a linear or branched C2-C20 alkynyl, comprising one or several triple bonds;

a saturated, partially or totally unsaturated C3-C7 cycloalkyl;

a halogen, preferably fluoride or chloride, provided that there is no halogen-heteroatom bond;

$NO_2$, provided that there is no bond of this group with a positively charged heteroatom, and that at least one R is different from $NO_2$;

CN, provided that there is no bond of this group with a positively charged heteroatom and that at least one R is different from CN;

wherein the R may be the same or different;

wherein pairs of R may be connected by single or double bonds;

wherein one or several R may be partially or totally substituted with halogens, preferably —F and/or —Cl, or partially with —CN or —$NO_2$, provided that not all R are totally halogenated;

and wherein one or two carbon atoms of any R may or may not be replaced by any heteroatom and/or group selected from the group of —O—, —C(O)—, —C(O)O—, —S—, —S(O)—, $SO_2$—, —S(O)$_2$O—, —N=, —P=, —NR'—, —PR'—, —P(O)(OR')—, —P(O)(OR')O—, —P(O)(NR'R')—, —P(O)(NR'R')O—, P(O)(NR'R')NR'—, —S(O)NR'—, and —S(O)$_2$NR', with R' being H, a C1-C6 alkyl, optionally partially or totally perfluorinated, and/or a phenyl, optionally partially or totally perfluorinated.

wherein any R is independently selected from H and C1-C15 alkyl.

Preferred substituents of the organic cations shown above are disclosed in WO2007/093961, on pages 5-7. The preferred cations defined on these pages are entirely incorporated herein by reference. The most preferred substituents R are independently selected from H and C1-C15 alkyl. Substituents are selected so that indicated positive charge is obtained.

Any alkyl, ankenyl or alkynyl referred to in this specification may be linear, branched or cyclic. Linear alkyls, alkenyls and alkynyls are preferred.

The electrolyte of the device of the invention may comprise two or more ionic liquids. Preferably, the electrolyte is substantially free of a solvent. Substantially free of a solvent means that there is less than 5 vol. % of added solvent, preferably no added solvent.

The counter electrode 7 is may comprise or consist of Pt, Au, Ni, Cu, Ag, In, Ru, Pd, Rh, Ir, Os, C, conductive polymer or a combination comprising two or more of the aforementioned. Examples of conductive polymers from which a suitable counter electrode material may be selected are polymers comprising polyaniline, polypyrrole, polythiophene, polybenzene and acetylene.

According to a preferred embodiment, the present invention provides a DSC comprising one or two transparent substrate layers 1, a conductive layer 2, a light absorption layer 3, a charge transport layer 6 and counter electrode 7. Said conductive layer 2, said light absorption layer 3, said electrolyte layer 6 and said counter electrode 7 are preferably connected in order, for example between two transparent substrate layers 1. The said light absorption layer 3 comprises a semiconductor nanoparticle layer 4 and a dye layer 5. The said semiconductor nanoparticle layer 4 is preferably connected with the said conductive layer 2 and the said dyes layer 5 is connected with the said charge transport layer 6.

The mentioned applications, patents, and publications in the context are listed and incorporated as references in the presented specification. It is supposed that technicians in this field can use the above description within the most extensive scope. Therefore, the optimal embodiment and examples are merely considered as an exemplary illustration and are in no way meant to constitute a restriction in any way.

The following examples are used for exemplary describing the preparation and synthesis of the compounds, organometallic compounds, dyes and/or sensitizers of the present invention. It does not mean that the scope of the invention is limited to these methods and applications.

EXAMPLES

Example 1: The Synthesis of Bipyridine Ligands

1. The Synthesis of 4,4'-bis(5-hexylfuran-2-yl)-2,2'-bipyridine (L1)

2-Hexylfuran was synthesized according to a literature method (Sheu, J.-H.; Yen, C.-F.; Huang, H.-C.; Hong, Y.-L. V. *J. Org. Chem.* 1989, 54, 5126). 2-Hexylfuran (2.20 g, 14.45 mmol) was dissolved in 40 mL of anhydrous THF and cooled to −78° C. After addition of n-butyllithium (Aldrich) (6.90 mL, 2.5 M in hexane, 17.34 mmol), the solution was stirred under Ar at −78° C. for 1 h. The mixture was stirred for 3 h at 20° C. and then cooled to −78° C. Tributylstannyl chloride (6.12 g, 18.80 mmol) in 10 mL of anhydrous THF was added dropwise via a syringe and stirred for 2 h at −78° C. The mixture was stirred overnight at room temperature. The reaction mixture was quenched with aqueous $NH_4Cl$ and extracted with $CH_2Cl_2$. The combined organic layers were dried over $MgSO_4$. After the removal of solvent, the unpurified 2-hexyl-5-tributylstannylfuran (4.22 g, 9.55 mmol) and 4,4'-dibromo-2,2'-bipyridine (1.00 g, 3.18 mmol) were dissolved in 120 mL of DMF. A catalytic amount of $Pd(PPh_3)_2Cl_2$ (0.13 g, 0.16 mmol) was added and the reaction mixture was stirred at 85° C. under Ar overnight. After the removal of DMF, the resulting solid was passed through a silica gel column using $CHCl_3$ as eluent to afford L1 (1.12 g, 77% yield) as yellowish solid. $_1$H NMR (600 MHz, $CDCl_3$, $\delta_H$): 8.66 (dd, J) 5.2 Hz, J) 0.6 Hz, 2H), 8.61 (s, 2H), 7.54 (dd, J) 5.2 Hz, J) 1.6 Hz, 2H), 6.93 (d, J) 2.8 Hz, 2H), 6.13 (d, J) 3.2 Hz, 2H), 2.72 (t, J) 7.6 Hz, 4H), 1.75-1.67 (m, 4H), 1.44-1.31 (m, 12H), 0.90 (t, J) 7.0 Hz, 6H). MS (EI) m/z calcd for ($C_{30}H_{36}N_2O_2$), 456.62. found, 456.

2. The Synthesis of 5-octylthieno[3,2-b]thiophene

To a stirred solution of thieno[3,2-b]thiophene (10.7 mmol) in anhydrous $CH_2Cl_2$ (200 mL) was added octanoyl chloride (11.0 mmol). The mixture was stirred for 30 min at room temperature, cooled to 0° C., and $AlCl_3$ (12.0 mmol) was added portionwise. The mixture was then warmed to 25° C. and stirred overnight. The reaction was quenched by the addition of water and acidified with a 2 M HCl aqueous solution. The mixture was extracted with $CH_2Cl_2$. The organic layers were washed with water and dried over $MgSO_4$. After the removal of solvent, the crude product was purified by column chromatography ($CH_2Cl_2$/n-hexane: 1/1) on silica gel to afford 1-(thieno[3,2-b]thiophen-2-yl)octan-1-one (2.08 g) as milk white solid. Yield: 72%. $_1$H NMR (400 MHz, $CDCl_3$, $^{TM}_H$): 7.90 (s, 1H), 7.61 (d, 1H), 7.30 (d, 1H), 2.92 (t, 2H), 1.81↕1.74 (m, 2H), 1.37↕1.30 (m, 8H), 0.88 (t, 3H). Cold anhydrous ether (100 mL) was added to separate batches of $LiAlH_4$ (58.0 mmol) and $AlCl_3$ (13.5 mmol) and the resulting suspended solutions were carefully mixed. To this mixture was added 1-(thieno[3,2-b]thiophen-2-yl)octan-1-one (6.0 mmol) in dry ether at 0° C. The mixture was warmed to room temperature and then stirred for 3 h. The reaction was quenched by the careful addition of ether and a 2 M HCl aqueous solution. The gray precipitate was filtrated and washed with ether. The combined filtrate was extracted, washed with water, and dried over $MgSO_4$. After rotary evaporation of solvent, the crude product was purified with column chromatography (n-hexane) on silica gel to afford white solid. (1.46 g). Yield: 96%. $_1$H NMR (400 MHz, $CDCl_3$, $^{TM}_H$): 7.27 (d, 1H), 7.18 (d, 1H), 6.95 (s, 1H), 2.87 (t, 2H), 1.73↕1.53 (m, 2H), 1.39↕1.27 (m, 10H), 0.88 (t, 3H).

3. The Synthesis of 4,4'-bis(5-octylthieno[3,2-b]thiophen-2-yl)-2,2'-bipyridine (L2)

n-Butyllithium (6.94 mmol) was slowly added dropwise to a solution of 5-octylthieno[3,2-b]thiophene (5.94 mmol) in anhydrous THF at ↕78° C. under Ar. The mixture was stirred at this temperature for 30 min and then for 1.5 h at room temperature followed, after cooling to ↕78° C., by the addition of tributylstannyl chloride (7.52 mmol). After stirring for 4 h at room temperature, the reaction was terminated by adding a saturated $NH_4Cl$ aqueous solution. The mixture was extracted with $CH_2Cl_2$ and dried over $MgSO_4$. After the removal of solvent, the crude tributyl(5-octylthieno[3,2-b]thiophen-2-yl)stannane (5.2 mmol) was mixed with 4,4'-dibromo-2,2'-bipyridine (1.72 mmol) in 150 mL DMF. The catalyst $Pd(PPh_3)_2Cl_2$ (0.08 mmol) was added to the solution and the mixture was heated at 85° C. under Ar overnight. After the removal of DMF, the resulting solid was purified by column chromatography on silica gel using $CHCl_3$ as eluent to afford an ivory white solid. Yield: 74%. $_1$H NMR (400 MHz, $CDCl_3$, $^{TM}_H$): 8.73 (s, 2H), 8.67 (d, 2H), 7.84 (s, 2H), 7.52 (d, 2H), 6.99 (s, 2H), 2.90 (t, 4H), 1.76↕1.72 (m, 4H), 1.41↕1.28 (m, 20H), 0.89 (t, 6H). MS (EI) m/z calcd. for $C_{38}H_{44}N_2S_4$: 657.03. Found: 657.24.

Example 2: Synthesis of Dyes According to the Invention

Scheme 1:

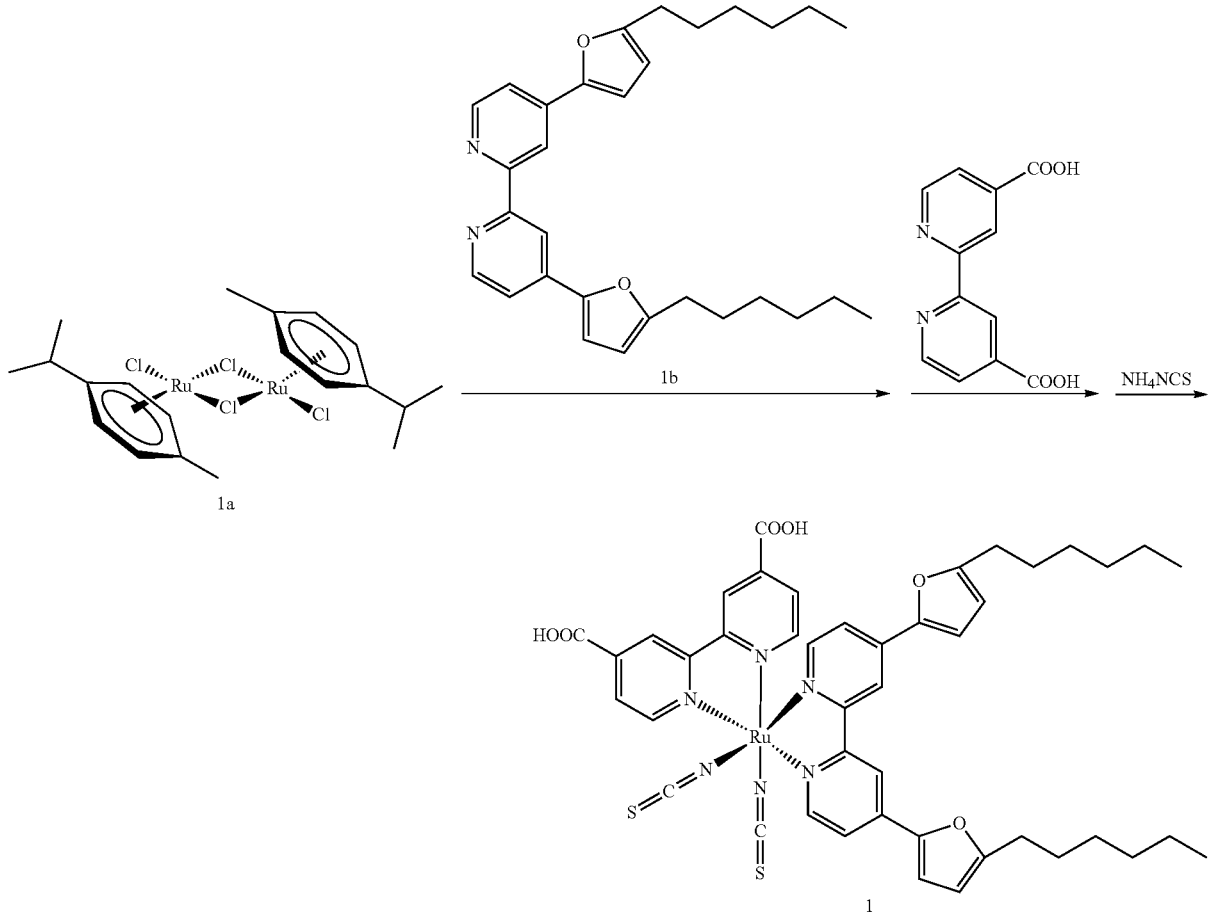

The synthetic approach for the preparation of the dyes of the present invention is illustrated by scheme 1 above, which will be used to describe in more detail the synthesis of dye (40) according to the present invention.

Compound 1a is obtained from Aldrich. Compound 1b corresponds to ligand L1 obtained in Example 1 (1.) above.

Compounds 1a (0.1 g, 0.16 mmol) and 1b (0.146 g, 0.32 mmol) were dissolved in DMF (50 mL). The reaction mixture was heated to 60° C. under nitrogen for 4 hours with constant stirring. To this reaction flask 4,4'-dicarboxylic acid-2,2'-bipyridine (0.08 g, 0.32 mmol) was added and refluxed for 4 hours at 140° C. Then an excess of NH$_4$NCS (0.89 g, 13 mmol) was added to the reaction mixture and the reflux was continued for another 4 hours at the same temperature. The reaction mixture was cooled down to room temperature and the solvent (DMF) was removed by using a rotary evaporator under vacuum. Water was added to the flask and the insoluble solid was collected on a sintered glass crucible by suction filtration, washed with water and EtO$_2$, and dried under vacuum. The crude was dissolved in a basic methanol solution (NaOH) and purified by passing through a column. After the collecting main band was concentrated, the pH was lowered to 4.8 by titration with dilute nitric acidic in methanol solution, which produced dye 20 as a precipitate. The precipitate was collected on a sintered glass crucible by suction filtration and dried in air. The following NMR data for dye 40 (with double sodium salt form) were obtained: $^1$H NMR (400 MHz, DMSO-d6): δ=0.83 (t, 3H), 0.89 (t, 3H), 1.26-1.42 (m, 12H), 1.62 (m, 2H), 1.75 (m, 2H), 2.70 (t, 2H), 2.83 (t, 2H), 6.41 (d, 1H), 6.53 (d, 1H), 7.28 (d, 1H), 7.37 (d, 1H), 7.43 (d, 1H), 7.61 (d, 1H), 7.87 (d, 1H), 8.06 (d, 1H), 8.32 (d, 1H), 8.70 (s, 1H), 8.86 (s, 1H), 8.94 (s, 1H), 9.10 (s, 1H), 9.13 (s, 1H), 9.45 (d, 1H).

The dyes of formulae (41)-(44) were synthesized using corresponding starting materials instead of 1b according to an analogues procedure. For example, by using the octylthieno[3,2-b]thiophen bipyridine ligand (L2) obtained in Example 1 (3.) above, instead of L1 of Example 1, dye (41) of the present invention is obtained.

Example 3: Preparation of a Dye-Sensitized Solar Cell Using the Sensitizing Dye of Formula (40)

A screen-printed double layer film of TiO$_2$ particles was used as photoanode. A 7 μm thick film of 20 nm sized TiO$_2$ particles was first printed on the fluorine-doped SnO$_2$ conducting glass electrode and further coated by a 5 μm thick second layer of 400 nm sized light scattering anatase particles. Fabrication procedure for nanocrystalline TiO$_2$ particles and photoanode with nanostructure double layers of TiO₂ has been reported. (Wang P. et al., Enhance the Performance of Dye-Sensitized Solar Cells by Co-grafting Amphiphilic Sensitizer and Hexadecylmalonic Acid on TiO₂ Nanocrystals, J. Phys. Chem. B., 107, 2003, 14336).

The TiO₂ electrodes were immersed into a solution containing 300 μM of dye (40), and, in another device, dye (41), in tert-butanol and acetonitrile (volume ratio 1:1) for 16 h.

Surprisingly, the dye molecules of the present invention, when absorbed on the TiO₂ exhibit a particularly pronounced red-shift, substantially increasing the spectrum of the light absorbed by the light-absorbing surface (here: TiO₂ and absorbed dye). This substantial increase in the red shift could not be expected from the light absorption spectrum of the dyes e in solution.

It is also derived that dye molecules are particularly densely arranged on the semiconductor surface. In conclusion, π-stacking of the dyes of the invention when absorbed on the surface explains the strong high absorption of light in the red part of the light spectrum and of the dense arrangement of dye molecules.

The double layered, nanocrystalline TiO₂ film electrode was assembled with a thermally platinized conducting glass electrode. The two electrodes were separated by a 35 μm thick hot-melt ring and sealed up by heating.

The internal space was filled with an electrolyte consisting of: 1.0 M 1,3-dimethylimidazolium iodide, 0.05 M LiI, 0.1 M guanidinium thiocyanate, 30 mM I₂, 0.5 M tert-butylpyridine in the mixture of the solvents acetonitrile and valeronitrile (85/15, v/v). After that, the electrolyte-injection hole was sealed. For the fabrication details see the reference of Wang P. et al., "A Solvent-Free, SeCN⁻/(SeCN)₃⁻ Based Ionic Liquid Electrolyte for High-Efficiency Dye-Sensitized Nanocrystalline Solar Cell", J. Am. Chem. Soc., 126, 2004, 7164.

The short circuit photocurrent density ($J_{sc}$), open circuit photovoltage ($V_{oc}$), and fill factor (ff) of the device with dye (20) under AM 1.5 full sunlight (100 mW/cm²) are 17.8 mA cm⁻², 725 mV, and 0.734, respectively, yielding an overall conversion efficiency (η) of 9.5%.

Further dye-sensitized solar cells were fabricated according to the method of Example 2, and the device characteristics are listed in Table 1 below.

TABLE 1

Photovoltaic device parameters of DSCs According to the Invention

| dye | Open-circuit photovoltage(mV) | Short-circuit photocurrent density (mA/cm²) | Fill factor ff | Conversion efficiency (%) |
|---|---|---|---|---|
| 40 | 725 | 17.80 | 0.734 | 9.5 |
| 41 | 760 | 17.87 | 0.776 | 10.5 |
| 44 | 728 | 18.33 | 0.752 | 10.0 |

With the other exemplary dyes (42) and (43) of the present invention, devices with similar and performance are obtained.

Without wishing be bound by theory, it is believed that the particularly positive results obtained with dye (41) is due to the increased π-stacking of the dye on the surface of the photoanode, which in is due to the high planarity of the bipyridine antenna ligand substituted with a substituted condensed system of thiophene rings. The present invention thus provides ways of increasing the propensity of dye molecules to arrange in an advantageous way on the semiconductor and/or photoelectrode surface.

The invention claimed is:

1. A dye of formula (35):

$$ML_1L_2(L_3)_2 \tag{35}$$

wherein:

M is a metal atom selected from Ru, Os, Ir, Re, Rh, and Fe;

$L_1$ is a ligand selected from the compounds of formula (1):

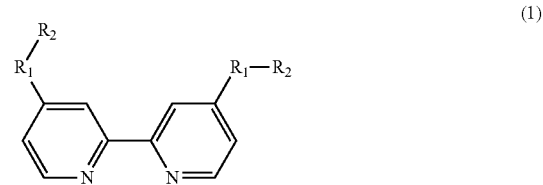

(1)

wherein $R_1$ is selected from the group consisting of the moieties of formulae (4)-(25) to (28)-(33):

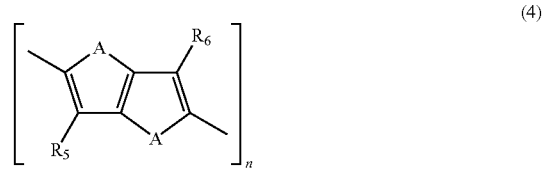

(4)

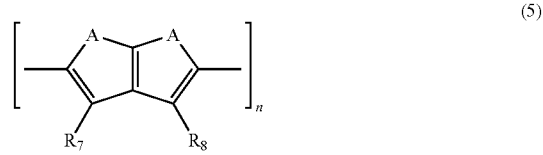

(5)

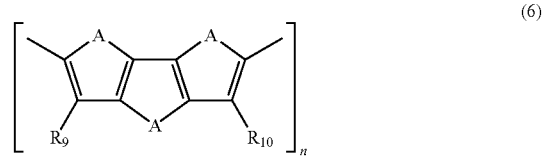

(6)

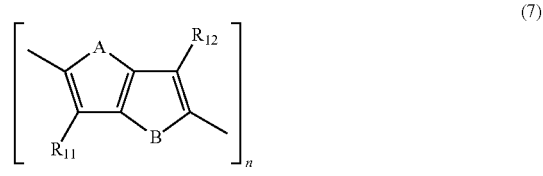

(7)

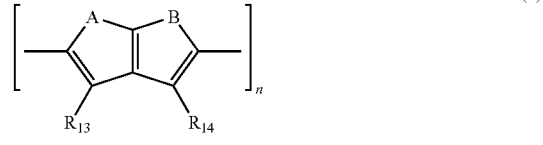

(8)

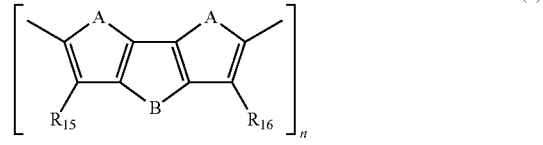

(9)

(10) 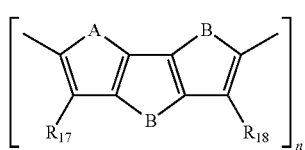
(11) 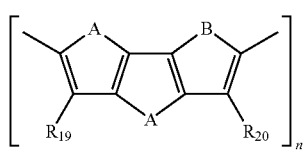
(12) 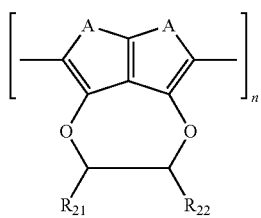
(13) 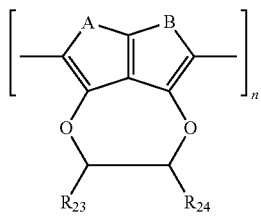
(14) 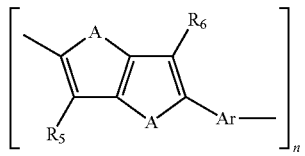
(15) 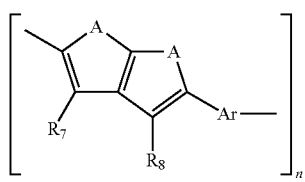
(16) 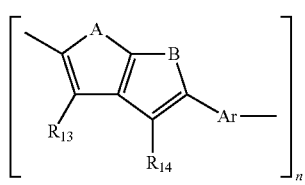
(17) 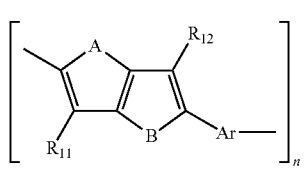
(18) 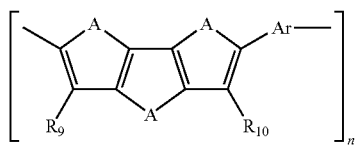
(19) 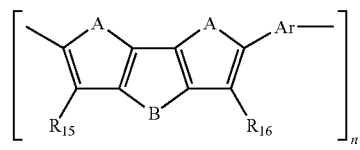
(20) 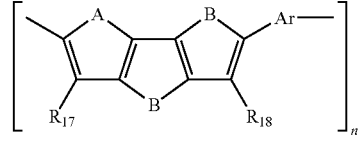
(21) 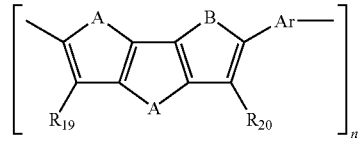
(22) 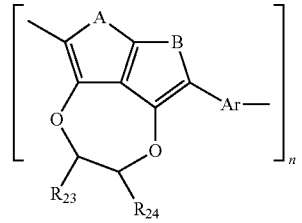
(23) 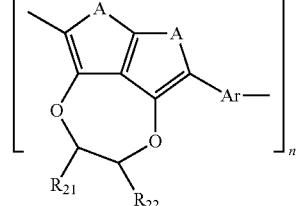
(24) 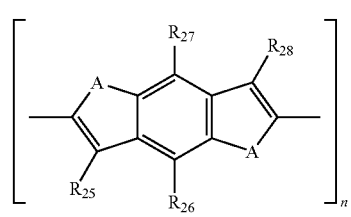
(25) 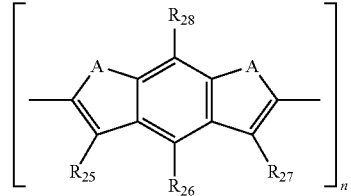
(28) 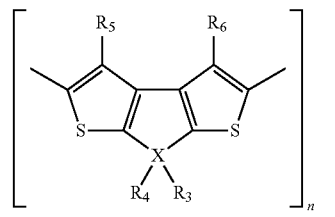

(29) 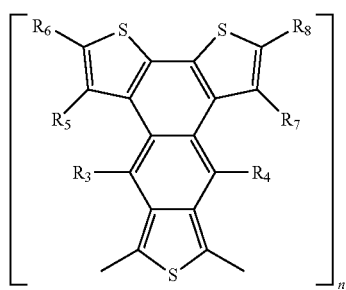

(30) 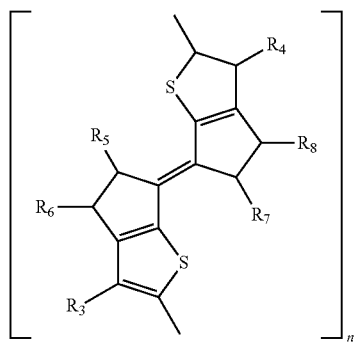

(31) 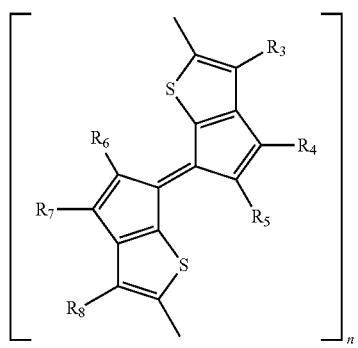

(32) 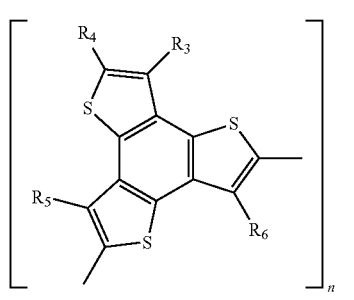

(33) 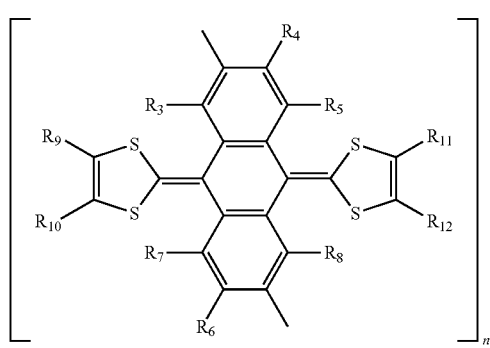

wherein n is ≥1;
wherein A of a moiety according to any one of formulae (4)-(6), (12), (14), (15), (18) and (23)-(25) is selected from O atom or S atom, each said A in a same moiety being selected from the same atom; and
wherein, in moiety according to any one of formulae (7)-(11), (13), (16), (17) and (19)-(22), A is selected from O atom and B is selected from S atom; or
wherein, in moiety according to any one of formulae (7)-(11), (13), (16), (17) and (19)-(22), A is selected from S atom and B is selected from O atom;
wherein, in moiety (28), X is selected from any one of C, Si, Ge, Sn or Pb;
wherein substituents $R_2$ represent, independently, hydrogen, halogen, hydroxyl, sulfhydryl, nitryl, cyanate, isocyanate, amine, acyl, carboxyl, sulfinyl, alkyl, alkenyl, alkynyl, and aryl, wherein said alkyl, alkenyl, alkynyl may be linear, branched or cyclic, and wherein said amine, acyl, carboxyl, sulfinyl, alkyl, alkenyl, alkynyl, and aryl may be further substituted, and
wherein one or more carbon atom in said alkyl, alkenyl, alkynyl, and aryl may be replaced by any heteroatom and/or group selected from the group of —O—, —C(O)—, —C(O)O—, —S—, —S(O)—, $SO_2$—, —S(O)$_2$O—, —N═, —P═, —NR'—, —PR'—, —P(O)(OR')—, —P(O)(OR')O—, —P(O)(NR'R')—, —P(O)(NR'R')O—, P(O)(NR'R')NR'—, —S(O)NR'—, and —S(O)$_2$NR', with R' being H, a C1-C6 alkyl, optionally partially or totally perfluorinated, and/or a phenyl or a monocyclic aromatic heterocycle, optionally partially or totally perfluorinated;
wherein Ar is a substituted or unsubstituted ar-diyl devoid of any heteroatom;
wherein $R_3$ to $R_{24}$ represent, independently, hydrogen, hydroxyl, alkyl, alkenyl, alkynyl, aryl, alkoxy, aryloxy, aralkyl, alkylthio, alkyl halide or halogen; and
wherein carbon atoms at positions 3, 3', 5, 5' and 6, 6' of the 2,2'-bipyridine structure of formula (1) may be further substituted;
$L_2$ is an anchoring ligand;
$L_3$ is a spectator ligand.

2. The dye according to claim 1, wherein said spectator ligand $L_3$ may be selected, independently, from the group consisting of $H_2O$, —Cl, —Br, —I, —CN, —NCO, —NCS and —NCSe.

3. The dye according to claim 1, wherein the anchoring ligand $L_2$ is a bi-pyridine compound of formula (36):

(36) 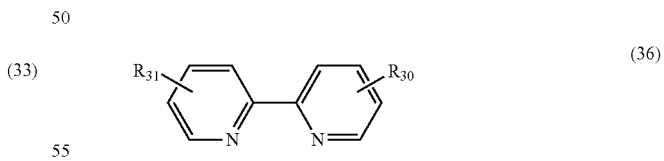

wherein $R_{30}$ and $R_{31}$ are independently selected from the group consisting of H, alkyl, alkenyl, alkynyl and aryl, said alkyl, alkenyl and/or aryl being substituted or unsubstituted, and from anchoring groups —COOH, —PO$_3$H$_2$, —PO$_4$H$_2$, —SO$_3$H$_2$, SO$_4$H$_2$, —CONHOH$^-$, acetylacetonate, deprotonated forms of the aforementioned and chelating anchoring groups with Π-conducting character; with the proviso that at least one of the substituents $R_{30}$ and $R_{31}$ comprises an anchoring group.

4. The dye according to claim 1, wherein $L_2$ is bi-pyridine ligand of formula (37)

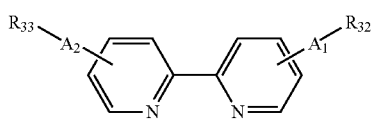
(37)

wherein $A_1$ and $A_2$ are optional and, if present, are independently selected from the group consisting of an aromatic mono- and bicyclic ring system optionally comprising one or more heteroatoms, and $R_{32}$ and $R_{33}$ are independently selected from H and from the anchoring groups —COOH, —PO$_3$H$_2$, —PO$_4$H$_2$, —SO$_3$H$_2$, SO$_4$H$_2$, —CONHOH, acetylacetonate, deprotonated forms of the aforementioned and chelating anchoring groups with Π-conducting character selected from an oxyme, dioxyme, hydroxyquinoline, salicylate and α-keto-enolate group, provided that at least one of $R_{32}$ and $R_{33}$ is an anchoring group.

5. The dye according to claim 1, which is compound (41) below:

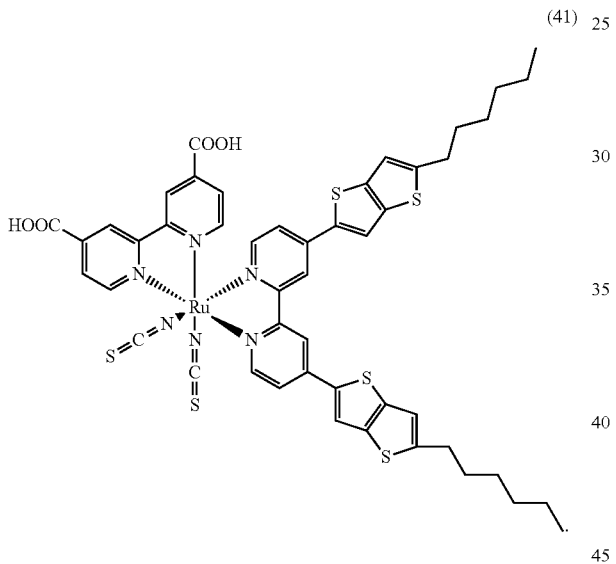
(41)

6. The dye according to claim 1, wherein $L_1$ is selected from the group consisting of a compound according to any one of formula (II), (III), (IV) and (VI) below:

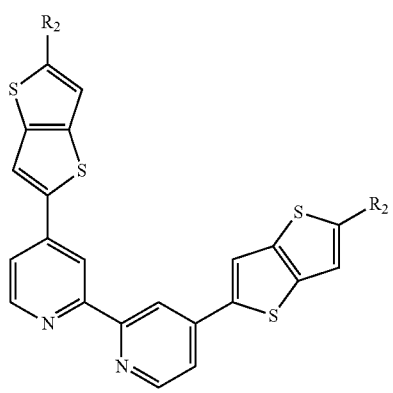
(II)

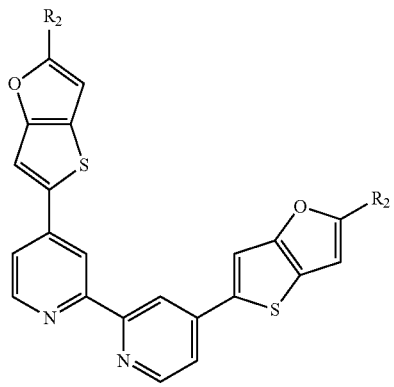
(III)

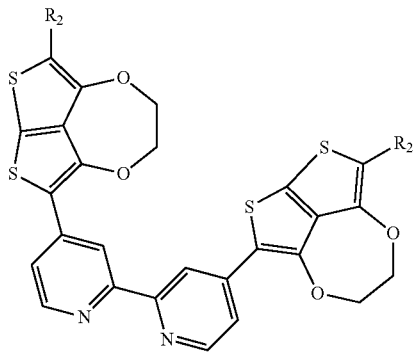
(IV)

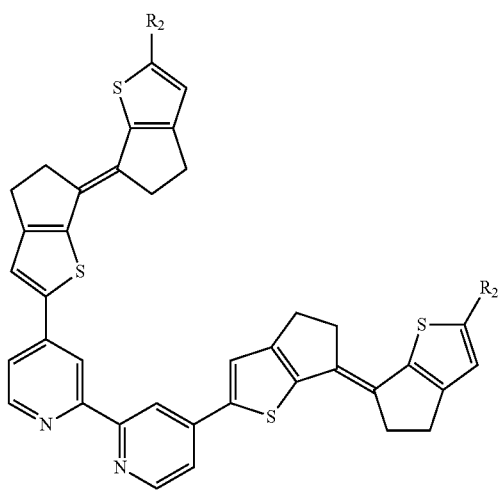
(VI)

wherein substituents $R_2$ represent, independently, hydrogen, halogen, hydroxyl, sulfhydryl, nitryl, cyanate, isocyanate, amine, acyl, carboxyl, sulfinyl, alkyl, alkenyl, alkynyl, and aryl, wherein said alkyl, alkenyl, alkynyl may be linear, branched or cyclic, and wherein said amine, acyl, carboxyl, sulfinyl, alkyl, alkenyl, alkynyl, and aryl may be further substituted, and wherein one or more carbon atom in said alkyl, alkenyl, alkynyl, and aryl may be replaced by any heteroatom and/or group selected from the group of —O—, —C(O)—, —C(O)O—, —S—, —S(O)—, SO$_2$—, —S(O)$_2$O—, —N=, —P=, —NR'—, —PR'—, —P(O)(OR')—, —P(O)(OR')O—, —P(O)(NR'R')—, —P(O)(NR'R')O—, P(O)(NR'R')NR'—, —S(O)NR'—, and —S(O)$_2$NR', with R' being H, a C1-C6 alkyl, optionally partially or totally perfluorinated, and/or a phenyl or a monocyclic aromatic heterocycle, optionally partially or totally perfluorinated.

7. The dye according to claim 1, wherein the anchoring ligand $L_2$ is a bi-pyridine compound of formula (36):

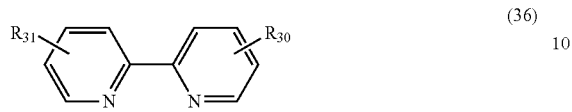

(36)

wherein $R_{30}$ and $R_{31}$ are independently selected from the group consisting of H, alkyl, alkenyl, alkynyl and aryl, said alkyl, alkenyl and/or aryl being substituted or unsubstituted, and from anchoring groups —COOH, —PO$_3$H$_2$, —PO$_4$H$_2$, —SO$_3$H$_2$, SO$_4$H$_2$, —CONHOH$^-$, acetylacetonate, deprotonated forms of the aforementioned and chelating anchoring groups with Π-conducting character; with the proviso that at least one of the substituents $R_{30}$ and $R_{31}$ comprises an anchoring group; and wherein said spectator ligand $L_3$ may be independently selected from the group consisting of H$_2$O, —Cl, —Br, —I, —CN, —NCO, —NCS and —NCSe.

* * * * *